United States Patent
Thiele et al.

(10) Patent No.: US 10,373,309 B2
(45) Date of Patent: Aug. 6, 2019

(54) METHOD TO SUPPORT TUMOR RESPONSE MEASUREMENTS

(71) Applicant: KONINKLIJKE PHILIPS N.V., Eindhoven (NL)

(72) Inventors: Frank Olaf Thiele, Aachen (DE); Martin Weibrecht, Aachen (DE)

(73) Assignee: Koninklijke Philips N.V., Eindhoven (NL)

( * ) Notice: Subject to any disclaimer, the term of this patent is extended or adjusted under 35 U.S.C. 154(b) by 113 days.

(21) Appl. No.: 15/028,738

(22) PCT Filed: Oct. 13, 2014

(86) PCT No.: PCT/IB2014/065252
§ 371 (c)(1),
(2) Date: Apr. 12, 2016

(87) PCT Pub. No.: WO2015/059600
PCT Pub. Date: Apr. 30, 2015

(65) Prior Publication Data
US 2016/0275676 A1    Sep. 22, 2016

Related U.S. Application Data

(60) Provisional application No. 61/894,457, filed on Oct. 23, 2013.

(51) Int. Cl.
*A61B 6/12* (2006.01)
*G06T 7/00* (2017.01)
(Continued)

(52) U.S. Cl.
CPC .......... *G06T 7/0012* (2013.01); *G06F 3/0485* (2013.01); *G06F 3/04812* (2013.01);
(Continued)

(58) Field of Classification Search
CPC ..... G06T 7/0012; G06T 7/50; G06F 3/04812; G06F 3/04845; G06F 3/0485
See application file for complete search history.

(56) References Cited

U.S. PATENT DOCUMENTS 6,112,112 A    8/2000  Gilhuijs et al.
7,876,939 B2   1/2011  Yankelevitz et al.
(Continued)

FOREIGN PATENT DOCUMENTS

EP      1614069 A      1/2006
JP   2011099142 A      5/2011
(Continued)

OTHER PUBLICATIONS

Eisenhauer, E.A. et al., New response evaluation criteria in solid tumours: European Journal of Cancer, Pergamon, vol. 45, No. 1, 2009, pp. 228-247.
(Continued)

*Primary Examiner* — Kim Y Vu
*Assistant Examiner* — Molly Delaney

(57) ABSTRACT

A method comprises the step of determining a minimum length of a lesion based on an imaging modality used to capture an image of the lesion and a slice thickness of the image, generating an extent cursor corresponding to the minimum size of the lesion, the extent cursor having a circular shape with a diameter corresponding to the minimum length and displaying the image of the lesion with the extent cursor positioned thereover.

22 Claims, 4 Drawing Sheets

(51) Int. Cl.
  *G06T 7/50* (2017.01)
  *A61B 5/107* (2006.01)
  *G06T 11/60* (2006.01)
  *G06F 3/0481* (2013.01)
  *G06F 3/0484* (2013.01)
  *G06F 3/0485* (2013.01)

(52) U.S. Cl.
  CPC ............ *G06F 3/04845* (2013.01); *G06T 7/50* (2017.01); *G06T 11/60* (2013.01); *A61B 5/1075* (2013.01); *A61B 6/12* (2013.01); *A61B 2576/00* (2013.01); *G06T 2207/10081* (2013.01); *G06T 2207/10088* (2013.01); *G06T 2207/10104* (2013.01); *G06T 2207/30096* (2013.01)

(56) References Cited

U.S. PATENT DOCUMENTS

| | | | |
|---|---|---|---|
| 8,401,260 | B2 | 3/2013 | Nirmal et al. |
| 2007/0027408 | A1 | 2/2007 | Fitzgerald et al. |
| 2007/0100226 | A1* | 5/2007 | Yankelevitz ......... A61B 5/1075 600/407 |
| 2010/0088644 | A1* | 4/2010 | Dowson ............... G06K 9/3233 715/837 |
| 2011/0026797 | A1* | 2/2011 | Declerck ............... G06T 7/0012 382/131 |
| 2011/0158491 | A1* | 6/2011 | Markova ............... G06T 3/0081 382/128 |
| 2012/0143623 | A1 | 6/2012 | Opfer et al. |
| 2014/0121524 | A1* | 5/2014 | Chiang .................. A61B 8/463 600/459 |
| 2018/0055468 | A1* | 3/2018 | Reicher .................. A61B 6/468 |

FOREIGN PATENT DOCUMENTS

| | | |
|---|---|---|
| JP | 2012105796 A | 6/2012 |
| WO | 2004088589 A1 | 10/2004 |
| WO | 2010074481 A2 | 7/2010 |
| WO | 2010086771 A1 | 8/2010 |
| WO | 2012090106 A1 | 7/2012 |
| WO | WO 2012090106 A1 * | 7/2012 ........... G06T 7/0012 |

OTHER PUBLICATIONS

Wahl, R. L. et al., "Standardization of Response Assessment: Methods, Analysis and Reporting: From RECIST to PERCIST 1.0", Division of Nuclear Medicine, Johns Hopkins Medical Institutes, Baltimore, MD, 2010.

Nensa, F., Dr., "Mint Lesion 2.0 Comprehensible Treatment Assessment in Radiology and Oncology", Mint Medical, 2013.

* cited by examiner

METHOD TO SUPPORT TUMOR RESPONSE MEASUREMENTS

CROSS-REFERENCE TO PRIOR APPLICATIONS

This application is the U.S. National Phase application under 35 U.S.C. § 371 of International Application No. PCT/IB2014/065252, filed on Oct. 13, 2014, which claims the benefit of U.S. Provisional Application No. 61/894,457, filed on Oct. 23, 2013. These applications are hereby incorporated by reference herein.

BACKGROUND

The treatment of tumors calls for the imaging of a target treatment area prior to and after administration of a treatment. A comparison of the two or more images is then carried out to assess an efficacy of the treatment. Procedures have been standardized to measure tumors in medical images from computed tomography (CT), magnetic resonance imaging (MRI) and positron emission tomography (PET). One such standardized procedure is response evaluation criteria in solid tumors (RECIST), which defines particular measurement criteria for each of the imaging modalities (e.g., PERCIST for PET, etc.) or tumor entities (e.g., Revised Assessment in Neuro-Oncology (RANO) for brain tumors, etc.). Most standardized procedures require a minimum tumor size, known as a measurable lesion, before response criteria (e.g., treatment) can be applied. In order to assess the dimensions of the tumor, a clinician performs a line measurement of the lesion to determine if it meets the minimum size criteria, known in the art as a "measurable lesion". This adds time and mouse clicks to the workflow and is operator dependent, thereby increasing the possibility of user error. The radiologist also has to determine a slice thickness of the medical image to determine the minimum measurement criteria that applies thereto.

SUMMARY

A system and method for assessing a lesion comprising the steps of determining a minimum length of a lesion based on an imaging modality used to capture an image of the lesion and a slice thickness of the image, generating an extent cursor corresponding to the minimum size of the lesion, the extent cursor having a circular shape with a diameter corresponding to the minimum length and displaying the image of the lesion with the extent cursor positioned thereover.

BRIEF DESCRIPTION OF THE DRAWINGS

Several embodiments of the invention will be described in the following by way of example and with reference to the accompanying drawings in which.

DETAILED DESCRIPTION

The exemplary embodiments may be further understood with reference to the following description and appended drawings. The exemplary embodiments propose a system and method for measuring tumors in medical images obtained via CT, MRI, PET, or any other imaging modality known in the art. The exemplary system and method according to the invention provides a method to support a clinician, radiologist or other user in determining if a lesion is measurable (i.e., meets a minimum size criteria) and needs to be further examined or treated. Specifically, the system and method according to the exemplary embodiments provides a mouse cursor over the medical image, the mouse cursor conforming to a minimum dimension of a measurable lesion according to the selected standard (e.g., RECIST, PERCIST, etc.). The minimum extent of the mouse cursor is automatically selected by a computing device based on the type of imaging modality being used, a slice thickness of the image and any other criteria which may be useful including, but not limited to patient-specific data. The mouse cursor is displayed on a screen as one or both of an "extent cursor" displayed as a circular representation enclosing the lesion therein and an "extent scale" displayed as a scale bar of minimum extent length, as will be described in greater detail later on. The radiologist or other user uses the extent cursor or extent scale to quickly and accurately make an assessment of the lesion and diagnose the patient.

Figure 1:
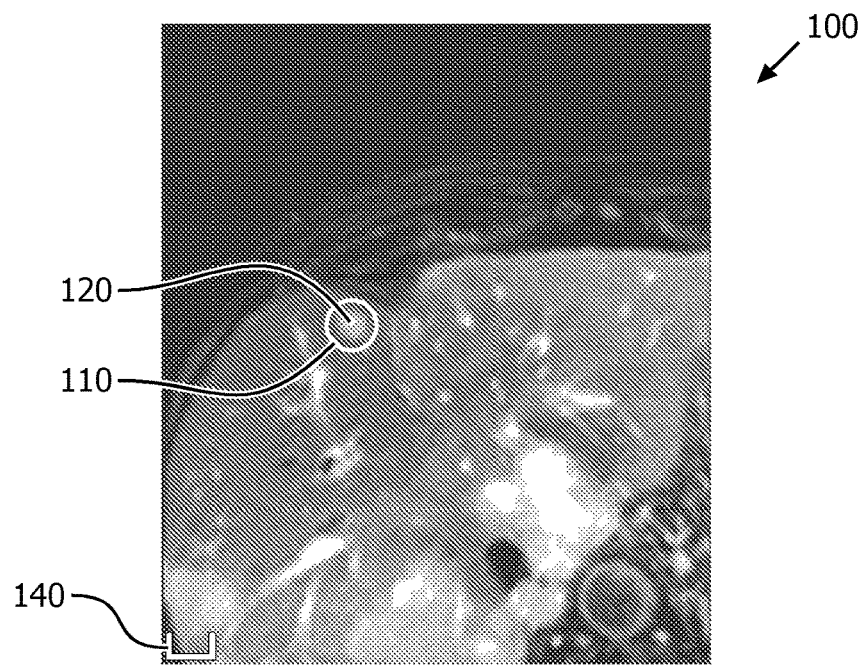
FIG. 1 depicts a $T_2$W-MRI image of a first lesion having an extent cursor and an extent scale provided thereon.

The exemplary embodiment is described in greater detail with respect to FIGS. 1-4. FIG. 1 depicts a first image 100 corresponding to a $T_2$-weighted MRI image of a liver lesion 120 captured with a 5 mm. slice thickness. The first image 100 is displayed on a display 408 of an exemplary system 400. A processor 406 of the system 400 automatically displays a first extent cursor 110 that may be moved in the display space represented by the first image 100. In an exemplary embodiment, the first extent cursor 110 is formed as a circular representation having a diameter conforming to a minimum diameter of a measurable lesion for a $T_2$-weighted MRI image captured with a 5 mm. slice thickness. In this example, the measurable lesion must meet or exceed a diameter of 10 mm. Thus, the first extent cursor 110 is formed as a circle having a 10 mm. diameter. The first extent cursor 110 is displayed over the first image 100 in a region containing a lesion 120. In one exemplary embodiment, the first extent cursor 110 may be automatically displayed in a previously input region of interest (e.g., corresponding to a location of the lesion 120 determined during an earlier imaging procedure). In another embodiment, the first extent cursor 110 may be manually positionable by the radiologist or other user over one or more lesions 120 displayed on the first image 100.

The first extent cursor 110 is provided in a predetermined, nonadjustable size. A color, line style and line thickness of the first extent cursor 110 may be selected to aid in viewing thereof over the first image. For example, the first extent cursor 110 may be formed with a solid line or dotted line. A color of the first extent cursor 110 is selected to contrast against a color of the first image 100 and may, for example, be red, blue, white, black or any other suitable color. In one exemplary embodiment, the radiologist or other user may change the color, line style or line thickness of the first extent cursor 110 via a user interface 410. The first extent cursor 110 may be automatically displayed on the display 408 or, in another embodiment, may be displayed only after prompted via the user interface 410. Still further, the radiologist may optionally display and remove the first extent cursor 110 via the user interface 410 to, for example, examine the lesion 120. In such an embodiment, the first extent cursor 110 is displayed on the same region of the first image 100, regardless of whether the first image 100 is resized, rotated, zoomed, etc. The radiologist may examine dimensions of the lesion 120 relative to the first extent cursor 110 and determine if the lesion 120 is equal to or greater than the minimum size requirement to qualify as a measurable lesion. In the present example, the lesion 120 is sufficient to be measurable.

In another embodiment, the first image 100 may be provided with an extent scale 140 that is shown on a lower border of the first image 100. It is noted that although the extent scale 140 is depicted on a lower border of the first image 100, the extent scale 140 may be provided along any border or anywhere else on the first image 100 without deviating from the scope of the disclosure. In another embodiment, the extent scale 140 may be positioned adjacent to the lesion 120 to aid in assessing a size thereof. In one embodiment, the extent scale 140 may be locked to a predetermined position on the displayed first image 100. In another embodiment, the extent scale 140 may be movable by the radiologist or other user to any desired location on the first image 100 and subsequently optionally locked in place. The extent scale 140 may be formed with a length corresponding to the minimum length of the measurable lesion. The extent scale may optionally also include a label (not shown) indicating a length thereof. Line properties of the extent scale 140 may be similar to those described above with respect to the first extent cursor 110 and may also be adjusted by a user via the user interface 410. The extent scale 140 may further be rotated via the user interface 410 to aid in measurement of the lesion 120, as those skilled in the art will understand. The first image 100 may be displayed with one or both of the first extent cursor 110 and the extent scale 140 automatically or upon being prompted via the user interface 410.

Figure 2:
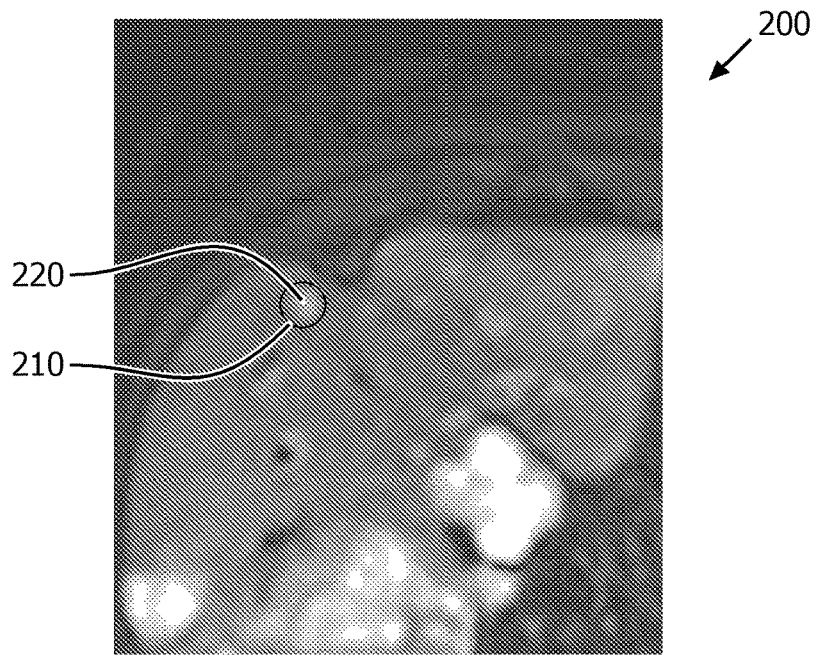
FIG. 2 depicts a DWI-MRI image of the first lesion having an extent cursor provided thereon.

FIG. 2 depicts a second image 200 according to another embodiment, the second image 200 corresponding to a diffusion weighted imaging (DWI) MRI of a liver lesion acquired with a 7 mm. slice thickness. A lesion 220 is highlighted by a second extent cursor 210, which has a diameter of 14 mm. The second extent cursor 210 clearly has a larger diameter than the lesion 220, thus indicating that the lesion 220 is not measurable in DWI MRI.

Figure 3:
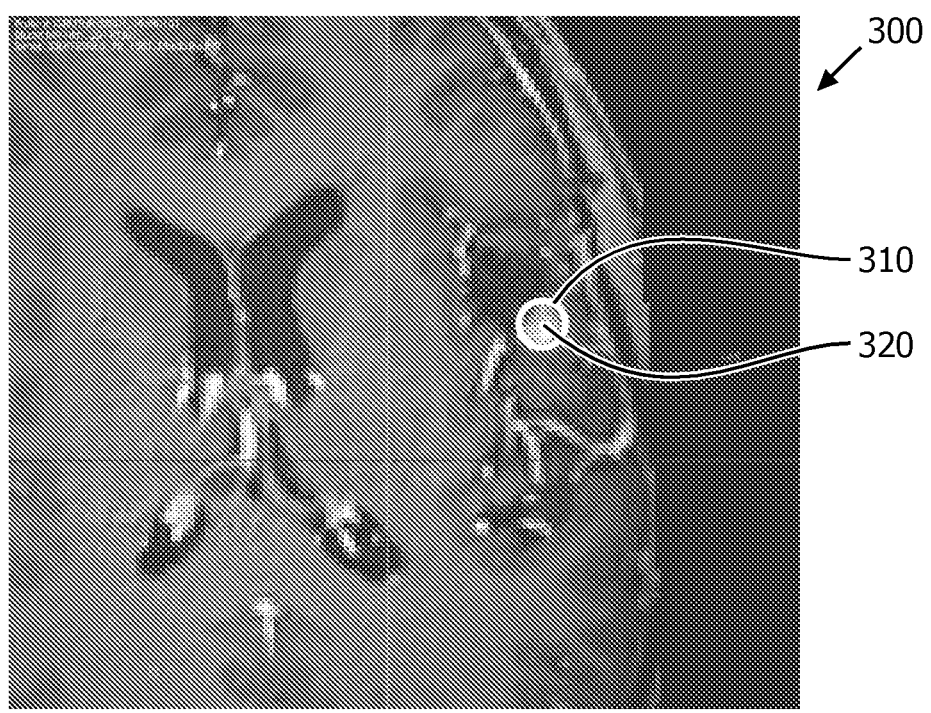
FIG. 3 depicts an MRI image of a second lesion having an extent cursor provided thereon.

FIG. 3 depicts a third image 300 according to another embodiment including a brain lesion 320 and a third extent cursor 310. The third extent cursor 310 is displayed as a white circular representation.

In another embodiment, the radiologist or other user may scroll through two or more images to assess a change in a lesion over time. In this embodiment, the first, second, or third extent cursor 110, 210, 310 may remain in position over the lesion 120, 220, 320 while the user toggles between the plurality of images. The plurality of images may also be displayed side by side on a single display with their respective extent cursors and/or extent scales to aid in a visual comparison thereof.

Figure 4:
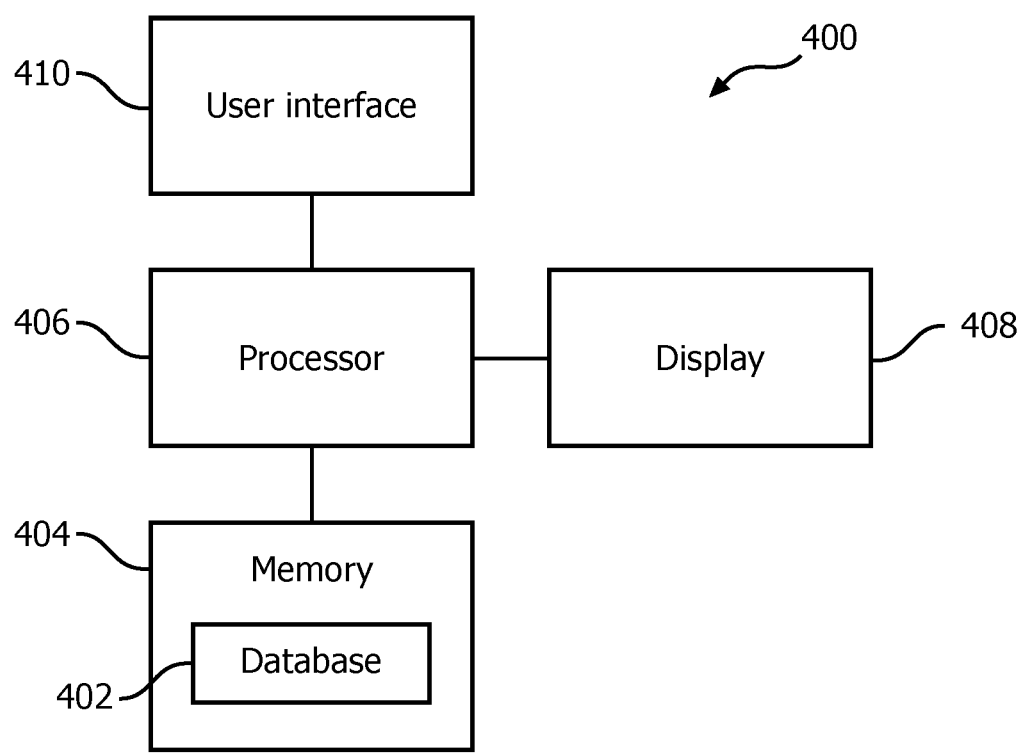
FIG. 4 shows a schematic drawing of a system according to an exemplary embodiment.
Figure 5:
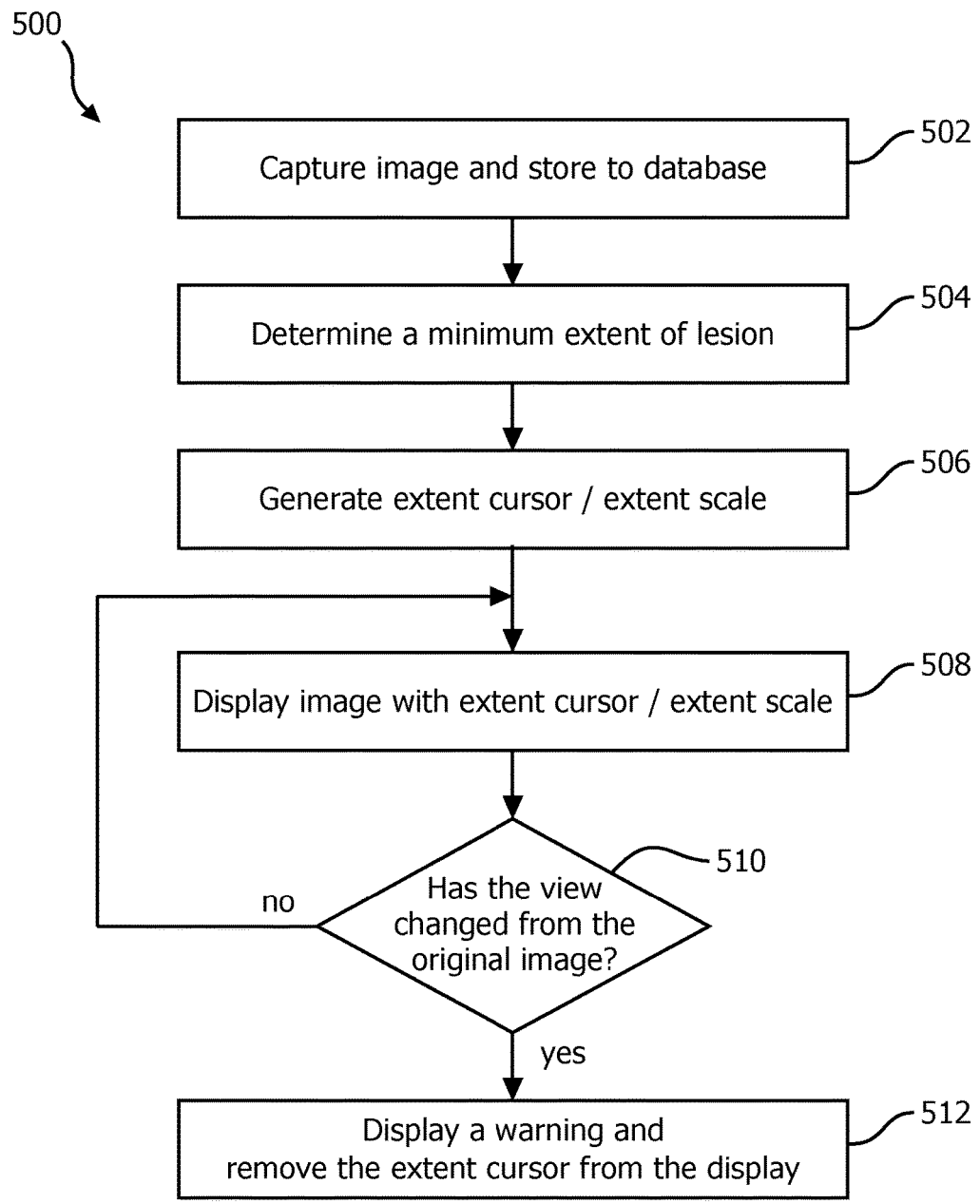
FIG. 5 depicts a flow diagram of an exemplary method.

FIGS. 4-5 depict the exemplary system 400 and method 500 according to the disclosure. In a first step 502, first, second, or third image 100,200,300 is captured and stored on a database 402 of a memory 404. As those skilled in the art will understand, the first step 502 may be optionally omitted and a processor 406 may reference first, second, or third image 100, 200, 300 previously stored on the database 402. In step 504, the processor 406 determines a minimum extent of a lesion based on the imaging modality used and the slice thickness thereof. The processor 406 may use an algorithm to determine the minimum extent as defined by tumor response standards. Specifically, for RECIST 1.1, the extent of a tumor lesion is determined as follows:

for CT and MRI: ≥min(10 mm, 2×(slice thickness+slice gap))
for chest x-ray: ≥20 mm
for lymph node assessment: ≥15 mm For brain tumors (RANO criteria), two perpendicular diameters of the minimum extent have to be present. However, the minimum extent itself is determined with the same criteria as noted above with respect to RECIST. It is noted that although the present embodiment has been described with respect to a predetermined algorithm defining requirements of the measurable lesion, any other standards may be used without deviating from the scope of the disclosure. In one example, a radiologist or other user may manually enter, via the user interface 410, the minimum length of the lesion. In particular, the user may override the automatically determined extent if necessary. Furthermore, details of the first, second, or third image 100,200,300 including imaging modality and slice thickness may be derived from the image data (e.g., via DICOM tags) itself or may also be manually entered by the user.

In step 506, the processor 406 generates one or both of the first, second, or third extent cursor 110, 210, 310 and the extent scale 140. In step 508, the processor 406 displays the first, second, or third image 100,200,300 with the corresponding first, second, or third extent cursor 110, 210, 310 and/or extent scale 140 on a display 408. A radiologist or other user may manipulate, scroll through or otherwise edit any of the first, second, or third images 100, 200, 300 via the user interface 410 which may include any of a keyboard, mouse and/or a touch display on the display 408. The user may also change the display to view a different image other than the first, second, or third image 100,200,300 for which the extent cursor 110 was formulated. To enforce RECIST guidelines, additional consistency checks and warnings may optionally be imposed as in optional step 510. Specifically, the minimum extent of the lesion is defined in the acquired 2D imaging plane. Therefore, the first, second, or third extent cursor 110, 210, 310 and extent scale 140 are only shown for in-plane viewing. In step 510, the processor 406 determines if other views (e.g., reformatted views) are currently being displayed on the display 408. If so, the method moves to step 512 wherein the first, second, or third extent cursor 110, 210, 310 is removed from the display and a warning is displayed to the user indicating that the extent cursor 110 is not applicable to the image currently being viewed.

The exemplary system and method disclosed herein may be employed with several commercial software products (e.g., Philips IntelliSpace—Tumor Tracking, Mint Lesion, etc.)

Although the invention has been described with two-dimensional imaging, any other image analysis technique may be used without deviating from the scope of the invention. For example, the image analysis may include 3-dimensional imaging wherein the extent cursor may comprise a sphere positioned in the 3-dimensional representation.

It will be appreciated by those skilled in the art that various modifications and alterations of the invention can be made without departing from the broad scope of the appended claims. Some of these have been discussed above and others will be apparent to those skilled in the art.

The invention claimed is:
1. A method, comprising:
   determining a minimum length of a measurable lesion according to a selected standard based on an imaging modality used to capture an image of a lesion and a slice thickness of the image;

generating an extent cursor conforming with the minimum length of the measurable lesion according to the selected standard, the extent cursor having a circular shape with a diameter corresponding to the minimum length; and displaying the image of a lesion with the extent cursor positioned thereover.

2. The method of claim 1, wherein the extent cursor is automatically displayed on the image.

3. The method of claim 1, wherein a position of the extent cursor on the image is adjustable via a user interface.

4. The method of claim 1, further comprising the step of operating a user interface to remove the extent cursor from a display.

5. The method of claim 4, further comprising the step of operating a user interface to display an extent scale over the image, the extent scale having a length corresponding to the minimum length.

6. The method of claim 5, wherein the extent scale may be positioned and rotated via the user interface.

7. The method of claim 1, further comprising the step of closing the image and displaying an additional image of the lesion.

8. The method of claim 7, wherein when the additional image is displayed, the extent cursor is removed and a warning is generated.

9. The method of claim 7, wherein the additional image including one or both of an additional extent cursor and an additional extent scale selected to conform to imaging specification of the additional image.

10. The method of claim 1, wherein a plurality of images is displayed side by side on a single display with their respective extent cursors and/or extent scales.

11. The method of claim 1, wherein the image is three-dimensional and the extent cursor is spherical.

12. The method of claim 1, wherein a predetermined algorithm is used to determine the minimum length of the measurable lesion.

13. The method of claim 1, wherein the imaging modality is one of: computer tomography (CT), a magnetic resonance imaging (MRI), an X-ray, and a lymph node assessment.

14. The method of claim 1, wherein the selected standard is one of: response evaluation criteria in solid tumors (RECIST), positron emission response criterial in solid tumors (PERCIST); and Revised Assessment in Neuro-Oncology (RANO).

15. The method of claim 1, wherein the extent cursor has a nonadjustable size.

16. A system for assessing lesions, comprising:

a processor for determining a minimum length of a measurable lesion according to a selected standard based on an imaging modality used to capture an image of the lesion and a slice thickness of the image, the processor being further configured for generating an extent cursor conforming with the minimum length of the measurable lesion according to the selected standard, the extent cursor having a circular shape with a diameter corresponding to the minimum length and displaying the image of a lesion with the extent cursor positioned thereover.

17. The system of claim 16, wherein the processor permits scrolling through an additional image of the measurable lesion with the extent cursor remaining in position over the measurable lesion while a user toggles between a plurality of images.

18. The system of claim 16, wherein the imaging modality is one of: computer tomography (CT), a magnetic resonance imaging (MRI), an X-ray, and a lymph node assessment.

19. The system of claim 16, wherein the selected standard is one of: response evaluation criteria in solid tumors (RECIST), positron emission response criterial in solid tumors (PERCIST); and Revised Assessment in Neuro-Oncology (RANO).

20. The system of claim 16, wherein the processor is further configured to generate an extent scale over the image, the extent scale having a length corresponding to the minimum length.

21. The system of claim 16, wherein the extent cursor has a nonadjustable size.

22. A non-transitory computer-readable storage medium including a set of instructions executable by a processor, the set of instructions operable to carry out the method of claim 1.

* * * * *